US00PP28420P2

(12) United States Plant Patent
Kobayashi

(10) Patent No.: US PP28,420 P2
(45) Date of Patent: Sep. 19, 2017

(54) **NEW GUINEA *IMPATIENS* PLANT NAMED 'DUESSPNEORED'**

(50) Latin Name: *Impatiens×hybrida*
Varietal Denomination: Duesspneored

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/999,697

(22) Filed: Jun. 16, 2016

(51) Int. Cl.
*A01H 5/02* (2006.01)

(52) U.S. Cl.
USPC ..... Plt./318.7

(58) Field of Classification Search
USPC ..... Plt./318.7
CPC ..... A01H 5/0261
See application file for complete search history.

*Primary Examiner* — Kent L Bell
(74) *Attorney, Agent, or Firm* — C. A. Whealy

(57) ABSTRACT

A new and distinct cultivar of *Impatiens* plant named 'Duesspneored' characterized by its upright, outwardly spreading and mounding plant habit; vigorous growth habit; freely branching habit; medium green-colored leaves; early and freely flowering habit; red-colored flowers; and good garden performance.

1 Drawing Sheet

Botanical designation: *Impatiens×hybrida.*
Cultivar denomination: 'DUESSPNEORED'.

BACKGROUND OF THE INVENTION

The present invention relates to a new and distinct cultivar of New Guinea *Impatiens* plant, botanically known as *Impatiens×hybrida* and hereinafter referred to by the name 'Duesspneored'.

The new *Impatiens* plant is a product of a planned breeding program conducted by the Inventor in Encinitas, Calif. The objective of the breeding program is to create new uniform *Impatiens* plants with numerous attractive flowers and good garden performance.

The new *Impatiens* plant is a naturally-occurring whole plant mutation of a proprietary selection of *Impatiens×hybrida* identified as code number NN-0028-X0012, not patented. The new *Impatiens* plant was discovered and selected by the Inventor as a single flowering plant from within a population of plants of the parent selection in a controlled greenhouse environment in Encinitas, Calif. on Apr. 26, 2015.

Asexual reproduction of the new *Impatiens* plant by terminal vegetative cuttings in a controlled greenhouse environment in Encinitas, Calif. since Jun. 12, 2015 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duesspneored'. These characteristics in combination distinguish 'Duesspneored' as a new and distinct *Impatiens* plant:

1. Upright, outwardly spreading and mounding plant habit.
2. Vigorous growth habit.
3. Freely branching habit.
4. Medium green-colored leaves.
5. Early and freely flowering habit.
6. Red-colored flowers.
7. Good garden performance.

Plants of the new *Impatiens* can be compared to plants of the parent selection. Plants of the new *Impatiens* differ primarily from plants of the parent selection in flower color as plants of the parent selection have dark orange-colored flowers.

Plants of the new *Impatiens* can be compared to plants of *Impatiens×hybrida* 'Misato FG3', disclosed in U.S. Plant Pat. No. 17,662. In side-by-side comparisons conducted in Encinitas, Calif., plants of the new *Impatiens* differed primarily from plants of 'Misato FG3' in the following characteristics:

1. Plants of the new *Impatiens* were more compact than plants of 'Misato FG3'.
2. Plants of the new *Impatiens* and 'Misato FG3' differed in leaf color as plants of 'Misato FG3' have darker green-colored leaves.
3. Plants of the new *Impatiens* and 'Misato FG3' differed in flower color as plants of 'Misato FG3' have magenta-colored flowers.

Plants of the new *Impatiens* can also be compared to plants of *Impatiens×hybrida* 'SAKIMP012', disclosed in U.S. Plant Pat. No. 19,392. In side-by-side comparisons conducted in Encinitas, Calif., plants of the new *Impatiens* differed primarily from plants of 'SAKIMP012' in the following characteristics:

1. Plants of the new *Impatiens* were more compact than plants of 'SAKIMP012'.

2. Plants of the new *Impatiens* and 'SAKIMP012' differed in leaf color as plants of 'SAKIMP012' have darker green-colored leaves.
3. Plants of the new *Impatiens* and 'SAKIMP012' differed in flower color as plants of 'SAKIMP012' have red purple-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet is a side perspective view of a typical flowering plant of 'Duesspneored' grown in a container.

The photograph at the top of the sheet is a close-up view of a typical flowering plant of 'Duesspneored'.

DETAILED BOTANICAL DESCRIPTION

The aforementioned photographs and following observations, measurements and values describe plants grown during the winter and spring in one-gallon containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 2,500 to 4,000 foot-candles. Plants were 20 weeks old when the photographs and description were taken. In the following description, color references are made to The Royal Horticultural Society Colour Chart, 2007 Edition, except where general terms of ordinary dictionary significance are used.

Botanical classification: *Impatiens×hybrida* 'Duesspneored'.

Parentage: Naturally-occurring whole plant mutation of a proprietary selection of *Impatiens×hybrida* identified as code number NN-0028-X0012, not patented.

Propagation:

*Type*.—By terminal cuttings.

*Time to initiate roots, summer and winter*.—About five to seven days at day temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to outwardly spreading and mounding plant habit; freely branching habit with about six primary branches each with about six lateral branches developing per plant; vigorous growth habit; moderate growth rate.

*Plant height*.—About 28 cm to 29 cm.

*Plant diameter*.—About 50 cm.

Lateral branch description:

*Length*.—Variable, longest branches are about 26 cm.

*Diameter*.—About 1.4 cm.

*Internode length*.—About 4.4 cm.

*Strength*.—Strong.

*Aspect*.—About 30° to 45° from vertical.

*Texture and luster*.—Smooth, glabrous; glossy.

*Color, developing*.—Close to 146B; at internodes, close to 146A.

*Color, developed*.—Close to 187A.

Leaf description:

*Arrangement*.—Opposite or in whorls; simple.

*Length*.—About 10 cm.

*Width*.—About 4.5 cm.

*Shape*.—Elliptical.

*Apex*.—Acuminate.

*Base*.—Attenuate.

*Margin*.—Entire with ciliation.

*Texture, upper and lower surfaces*.—Smooth, glabrous.

*Luster, upper surface*.—Semi-glossy.

*Luster, lower surface*.—Matte.

*Venation pattern*.—Pinnate; arcuate.

*Color*.—Developing leaves, upper surface: Close to 146A. Developing leaves, lower surface: Close to 146B. Fully opened leaves, upper surface: Close to N137A; venation, close to 147B to 147C. Fully opened leaves, lower surface: Close to 147B; venation, close to 147C to 147D.

*Petioles*.—Length: About 1.4 cm. Diameter: About 4 mm. Strength: Strong. Texture and luster, upper and lower surfaces: Smooth, glabrous; semi-glossy. Color, upper surface: Close to 177C. Color, lower surface: Close to 177D.

Flower description:

*Flower type and flowering habit*.—Single rounded and flat axillary flowers; freely flowering habit, typically about 160 flowers developing per plant during the flowering season; flowers positioned just above and beyond the foliar plane, flowers typically face mostly upright to outwardly.

*Flower longevity*.—Flowers typically last about two to three days on the plant under greenhouse conditions; petals self-cleaning, gynoecium persistent.

*Fragrance*.—None detected.

*Natural flowering season*.—In the garden, flowering from spring until fall in temperate regions; early flowering habit, plants typically begin flowering about nine weeks after planting.

*Flower buds*.—Length: About 1.9 cm. Diameter: About 1.3 cm. Shape: Ovoid, pointed. Texture and luster: Smooth, glabrous; slightly glossy. Color: Close to 53B.

*Flower diameter*.—About 4.6 cm by 4.8 cm.

*Flower depth*.—About 1.4 cm; including sepal spur, about 3 cm.

*Petals*.—Quantity and arrangement: Five per flower in a single whorl; one upper banner petal, two lateral petals and two lower petals. Length, banner petal: About 2.5 cm. Width, banner petal: About 3.5 cm. Length, lateral petals: About 2.5 cm. Width, lateral petals: About 2.4 cm. Length, lower petals: About 3.3 cm. Width, lower petals: About 3.2 cm. Shape: Cordate. Apex: Cordate; emarginate. Base: Attenuate. Margin: Entire. Texture, upper surface: Smooth, glabrous; velvety. Texture, lower surface: Smooth, glabrous; matte. Color: When opening, upper surface: Close to 46A. When opening, lower surface: Close to 53C. Fully opened, upper surface: Close to 46B; towards the base, close to 53A to 53B; venation, close to 46B; color does not change with development. Fully opened, lower surface: Close to 54A; venation, close to 54C; color does not change with development.

*Sepals*.—Quantity and arrangement: Three in a single whorl; one modified into an elongated spur. Length: About 1.1 cm. Width: About 7 mm. Shape: Elliptical. Apex: Acuminate. Base: Truncate. Margin: Entire. Texture and luster, upper and lower surfaces: Smooth, glabrous; slightly glossy. Color: When developing, upper surface: Close to 195D. When developing, lower surface: Close to 195A, 195B and 195C. Fully opened, upper surface: Close to 195B to 195C. Fully opened, lower surface: Close to 195B to 195C tinted with close to 185D. Spur length: About 6.1 cm. Spur diameter: At the flower, about 2.5 mm. Spur texture and luster: Smooth, glabrous; slightly glossy. Spur color: Close to 185B.

*Peduncles*.—Length: About 4.7 cm. Diameter: About 2 mm. Angle: About 45° from stem axis. Strength: Strong; flexible. Texture and luster: Smooth, glabrous; slightly glossy. Color: Close to 199D.

*Reproductive organs*.—Stamens: Quantity: Five fused at anthers; filaments free. Filament length: About 1 mm. Filament color: Close to 53B. Anther size: About 3 mm by 5 mm. Anther shape: Oblong. Anther color: Close to 53B. Pollen amount: Abundant. Pollen color: Close to 158A. Pistils: Quantity per flower: One. Pistil length: About 6 mm. Stigma diameter: About 1 mm. Stigma shape: Rounded. Stigma color: Close to 155A. Style color: Close to 146A. Ovary color: Close to 146A.

*Seeds and fruits*.—Seed and fruit production has not been observed on plants of the new *Impatiens*.

Disease & pest resistance: Plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Duesspneored' as illustrated and described.

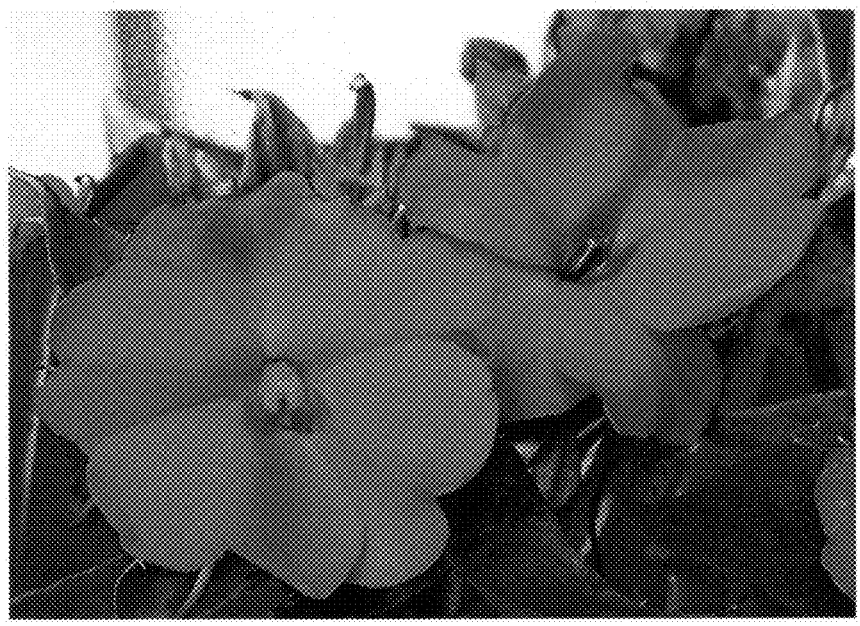
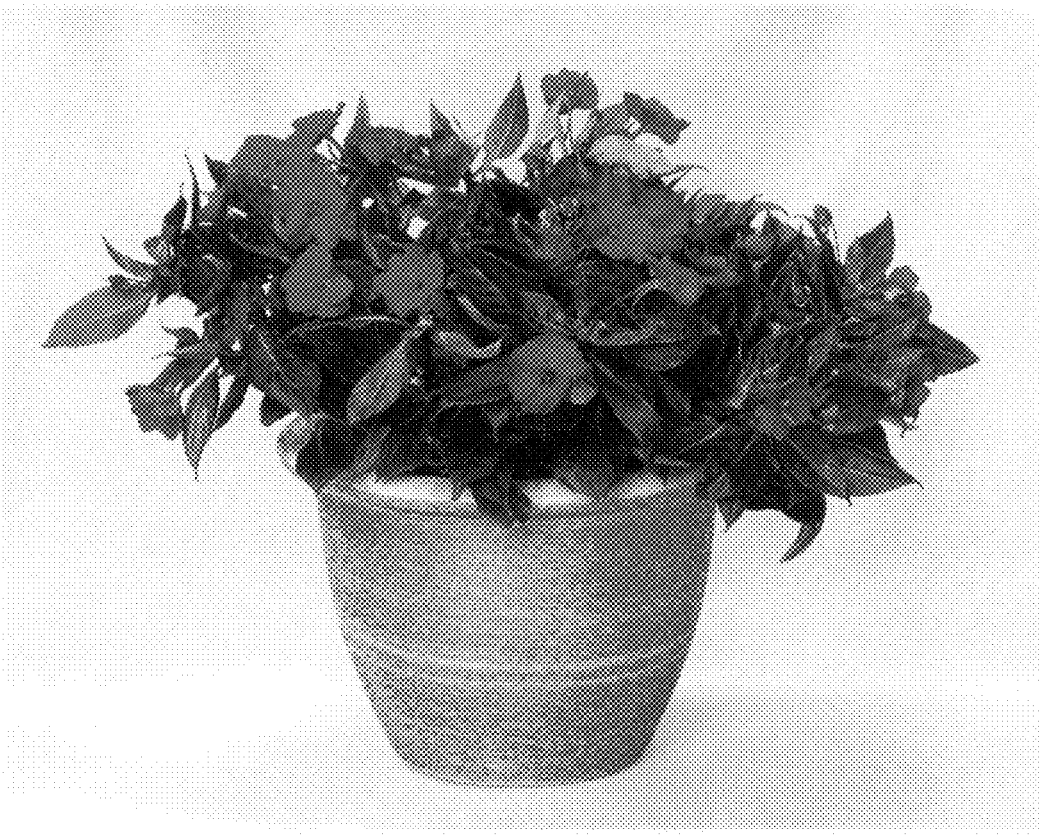

* * * * *